United States Patent [19]
Sawyer

[11] Patent Number: 5,669,934
[45] Date of Patent: Sep. 23, 1997

[54] METHODS FOR JOINING TISSUE BY APPLYING RADIOFREQUENCY ENERGY TO PERFORMED COLLAGEN FILMS AND SHEETS

[75] Inventor: Philip N. Sawyer, Brooklyn, N.Y.

[73] Assignee: Fusion Medical Technologies, Inc., Mountain View, Calif.

[21] Appl. No.: 461,228

[22] Filed: Jun. 5, 1995

Related U.S. Application Data

[63] Continuation of Ser. No. 370,552, Jan. 9, 1995, abandoned, which is a continuation of Ser. No. 7,691, Jan. 22, 1993, abandoned, which is a continuation-in-part of Ser. No. 832,171, Feb. 6, 1992, abandoned, which is a continuation-in-part of Ser. No. 654,860, Feb. 13, 1991, Pat. No. 5,156,613.

[51] Int. Cl.⁶ .................................................. A61H 5/06
[52] U.S. Cl. ........................... 606/213; 606/3; 606/7; 606/8; 606/10; 606/12; 606/17; 606/213; 606/214; 606/40; 606/215; 128/898
[58] Field of Search .................. 424/400; 606/7, 606/8, 10, 12, 17, 213, 214, 40, 3, 215; 128/898

[56] References Cited

U.S. PATENT DOCUMENTS

| | | | |
|---|---|---|---|
| 2,011,169 | 8/1935 | Wappler | 606/151 |
| 2,510,205 | 6/1950 | Baird | 219/8 |
| 2,618,267 | 11/1952 | Hanriot | 128/303.14 |
| 2,708,933 | 5/1955 | August | 128/303.14 |
| 2,808,833 | 10/1957 | Augard | 128/303.17 |

(List continued on next page.)

FOREIGN PATENT DOCUMENTS

| | | |
|---|---|---|
| 330 135 | 8/1989 | European Pat. Off. . |
| 405 429 | 2/1991 | European Pat. Off. . |
| 0 480 293 A1 | 4/1992 | European Pat. Off. . |
| 0 526 756 A1 | 2/1993 | European Pat. Off. . |
| 0 640 315 A1 | 3/1995 | European Pat. Off. . |

(List continued on next page.)

OTHER PUBLICATIONS

Khadem et al., "Photoynaic Biologic Tissue Glue", 1994, *Cornea*, vol. 13, No. 5, pp. 406–410.

Sensaki et al., "Laser Patch Welding: Experimental Study for Application to Endoscopic Closure of Bronchopleural Fistula, a Preliminary Report", 1995, *Laser in Surgery and Medicine*, vol. 16, pp. 24–33.

(List continued on next page.)

*Primary Examiner*—Raj Bawa
*Attorney, Agent, or Firm*—Townsend and Townsend and Crew LLP

[57] ABSTRACT

A method for joining or restructuring tissue consists essentially of providing a preformed film or sheet of a solid filler material which fuses to tissue upon the application of energy. The material comprises collagen, gelatin, mixtures thereof, optionally combined with a plasticizer, and the film may be cut prior to placing over the tissue. Radiofrequency energy is then applied at between about 20 and 120 Watts to the filler material and the tissue after the filler material has been placed over the tissue for about 1 to 60 seconds so that about 20 to 1800 joules are delivered to the filler material and tissue.

5 Claims, 14 Drawing Sheets

U.S. PATENT DOCUMENTS

| | | | |
|---|---|---|---|
| 3,527,224 | 9/1970 | Rabinowitz | 606/214 |
| 3,578,939 | 5/1971 | Green | 219/74 |
| 3,742,955 | 7/1973 | Battista | 606/214 |
| 3,834,392 | 9/1974 | Lampman et al. | 128/303.13 |
| 3,858,586 | 1/1975 | Lessen | 128/303.1 |
| 3,903,891 | 9/1975 | Brayshaw | 128/303.14 |
| 3,991,764 | 11/1976 | Incropera | 128/303.1 |
| 4,040,426 | 8/1977 | Morrison | 128/303.17 |
| 4,060,088 | 11/1977 | Morrison et al. | 606/303.17 |
| 4,100,390 | 7/1978 | Jackson | 219/74 |
| 4,122,853 | 10/1978 | Smith | 128/303.1 |
| 4,238,480 | 12/1980 | Sawyer | 424/177 |
| 4,618,885 | 10/1986 | Nagasaki | 358/98 |
| 4,633,870 | 1/1987 | Sauer | 128/303.1 |
| 4,638,800 | 1/1987 | Michel | 606/14 |
| 4,640,279 | 2/1987 | Beard | 128/303.14 |
| 4,672,969 | 6/1987 | Dew | 606/3 |
| 4,708,137 | 11/1987 | Tsukagoshi | 128/303.15 |
| 4,733,660 | 3/1988 | Itzkan | 606/17 |
| 4,781,175 | 11/1988 | McGreery et al. | 128/303.7 |
| 4,854,320 | 8/1989 | Dew et al. | 128/397 |
| 4,878,492 | 11/1989 | Sinofsky et al. | 128/303.1 |
| 4,889,120 | 12/1989 | Gordon | 606/7 |
| 4,892,098 | 1/1990 | Sauer | 606/8 |
| 4,901,719 | 2/1990 | Trenconsky et al. | 606/49 |
| 4,901,720 | 2/1990 | Bertrand | 606/40 |
| 4,929,246 | 5/1990 | Sinofsky | 606/3 |
| 4,930,504 | 6/1990 | Diamantopoulas et al. | 606/3 |
| 4,943,290 | 7/1990 | Rexroth et al. | 606/45 |
| 5,002,051 | 3/1991 | Dew | 606/12 |
| 5,021,452 | 6/1991 | Labbé et al. | 514/474 |
| 5,041,110 | 8/1991 | Fleenor | 606/34 |
| 5,071,417 | 12/1991 | Sinofsky | 606/8 |
| 5,140,984 | 8/1992 | Dew et al. | 606/11 |
| 5,201,745 | 4/1993 | Tayot et al. | 606/151 |
| 5,207,670 | 5/1993 | Sinofsky | 606/8 |
| 5,207,691 | 5/1993 | Nardella | 606/142 |
| 5,209,776 | 5/1993 | Bau et al. | 606/214 |
| 5,219,895 | 6/1993 | Kelman et al. | 522/68 |
| 5,272,716 | 12/1993 | Soltz et al. | 372/109 |
| 5,290,272 | 3/1994 | Burstein et al. | 606/4 |
| 5,292,253 | 3/1994 | Levy | 433/215 |
| 5,292,362 | 3/1994 | Bass et al. | 106/124 |
| 5,330,974 | 7/1994 | Pines et al. | 514/21 |
| 5,334,191 | 8/1994 | Poppas et al. | 606/12 |
| 5,336,221 | 8/1994 | Anderson | 606/27 |
| 5,354,323 | 10/1994 | Whitebook | 607/89 |
| 5,354,336 | 10/1994 | Kelman et al. | 623/6 |
| 5,372,585 | 12/1994 | Tiefenbrun et al. | 604/59 |
| 5,403,312 | 4/1995 | Yates et al. | 606/50 |
| 5,409,481 | 4/1995 | Poppas et al. | 606/12 |
| 5,410,016 | 4/1995 | Hubbell et al. | 528/354 |
| 5,421,923 | 6/1995 | Clarke et al. | 156/73.1 |

FOREIGN PATENT DOCUMENTS

| | | |
|---|---|---|
| 4-288165 | 10/1992 | Japan . |
| 1091933 | 5/1984 | U.S.S.R. . |
| 91/04073 | 4/1991 | WIPO . |
| 92/02238 | 2/1992 | WIPO . |
| WO 93/03793 | 3/1993 | WIPO . |
| WO 93/17669 | 9/1993 | WIPO . |

OTHER PUBLICATIONS

Kirsch et al., "Preliminary Results of Laser Tissue Welding in Extravesical Reimplantation of the Ureters", 1994, *The Journal of Urology*, vol. 151, pp. 514–517.

Poppas et al., "Preparation of Human Albumin Solder for Laser Tissue Welding", 1993, *Lasers in Surgery and Medicine*, vol. 13, pp. 577–580.

Poppas et al., "Chromophore Enhanced Laser Welding of Canine Ureters in Vitro Using a Human Protein Solder: A Preliminary Step for Laparoscopic Tissue Welding", 1993, vol. 150, pp. 1052–1055.

Poppas et al., "Patch Graft Urethroplasty Using Dye Enhanced Laser Tissue Welding With A Human Protein Solder: A Preclinical Canine Model", 1993, *The Journal of Urology*, vol. 150, pp. 648–650.

Wilder et al., "Skin Closure with Dye–Enhanced Laser Welding and Fibrinogen", 1991, *Plastic and Reconstructive Surgery*, vol. 88, No. 6, pp. 1018–1025.

Costello et al., "Sutureless End-to-End bowel Anastomosis Using Nd:YAG and Water–Soluble Intraluminal Stent," (1990), *Laser in Surgery and Medicine*, vol. 10, pp. 179–184.

Poppas et al., "Laser Welding in Urethral Surgery: Improved Results with a Protein Solder," (1988), *J. Urology*, vol. 139(2), pp. 415–417.

Barry et al., "The Effect of Radiofrequency—Generated Thermal Energy on the Mechanical and Histologic Characteristics of the Arterial Wall In Vivo," Rad. Ang., vol. 117, No. 2, pp. 332–341, 1989.

Bass et al., "Anastomosis of Biliary Tissue with High–Frequency Electrical Diathermy," Surgical Endoscopy, vol. 4, No. 2, pp. 94–96, 1990.

Bass et al., "Sutureless Microvascular Anastomosis Using the THC:YAG Laser: a Preliminary Report," Microsurgery, vol. 10, pp. 189–193, 1989.

Becker et al., "Radiofrequency Balloon Angioplasty Rationale and Proof of Principle", Invest. Rad., vol. 23, No. 11, pp. 810–817, 1988.

Benke et al., "Comparative Study of Suture and Laser–Assisted Anastomoses in Rat Sciatic Nerves," Lasers in Surgery and Medicine, 9:602–615 (1989).

Chemical Abstracts, vol. 114, No. 5, 38993y (1990).

Chuck et al., "Dye–Enhanced Laser Tissue Welding", Lasers in Surgery and Medicine, vol. 9, pp. 471–477 (1989).

Dennis et al., "Evaluation of Electrofulguration in Control of Bleeding of Experimental Gastric Ulcers", Digestive Diseases and Sciences, vol. 24, No. 11, pp. 845–848, Nov. 1979.

Hendry et al., "Argon Beam Coagulation Compared with Cryoablation of Ventricular Subendocardium," Ann. Thorac. Surg. vol. 55, pp. 135–139, 1993.

Komerska et al., "Collagen Films as Test Surfaces for Skin —Contact Pressure Adhesives," 1990.

Lee et al., "Thermal Compression and Molding of Atherosclerotic Vascular Tissue with Use of Radiofrequency Energy", JACC vol. 13, No. 5, pp. 1167–1175, Apr. 1989.

Libutti et al., "Canine Colonic Anastomoses Reinforced with Dye–Enhanced Fibrinogen and a Diode Laser", Surgical Endoscopy, vol. 4, No. 2, pp. 97–99 (1990).

Oz et al., "A Fiberoptic Compatible Midinfrared Laswer with $CO_2$ Laser–like Effect: Application to Atherosclerosis," Journal of Surgical Research, vol. 17, No. 6, pp. 439–501 (1989).

Oz et al., "Effects of a 2.15 –Micron Laser on Human Atherosclerotic Xenograft in Vivo", Angiology, The Journal of Vascular Diseases, vol. 41, pp. 772–776 (1990).

Oz et al., "In Vitro Comparison of Thulium–Holmium-–Chromium: YAG and Argon Ion Lasers for Welding of Biliary Tissue," Lasers in Surgery and Medicine, vol. 9, pp. 248–253 (1989).

Oz et al., "Strength of Laser Vascular Fusion: Preliminary Observations on the Role of Thrombus," Lasers in Surgery and Medicine, vol. 10, pp. 3939–395 (1990).

Oz et al., "Tissue Soldering by Use of Indocyanine Green Dye–Enhanced Fibrinogen with the Near Infrared Diode Laser," Journal of Vascular Surgery, vol. 11, No. 5, pp. 718–725, (1990).

Pachence et al., "Collagen: Its Place in the Medrail Device Industry," Jan. 1987.

Popp et al., "Welding of Gallbladder Tissue with a Pulsed 2.15 μm Thulium–Holmium–Chromium:YAG Laser," Lasers in Surgery and Medicine, 9:155–159 (1989).

Shapiro et al., "Microvascular End–To–Side Arterial Anastomosis Using the ND; YAG Laser," Neurosurgery, vol. 25, No. 4 (1989) pp. 584–589.

Treat et al., "Preliminary Evaluation of a Pulsed 2.15 μm Laser System for Fiberoptic Endoscopic Surgery," Lasers in Surgery and Medicine, vol. 8, pp. 322–326 (1988).

Oz et al. (1990), SPIE vol. 1200 (Program in Biomedical Optics), pp. 55–59.

METHODS FOR JOINING TISSUE BY APPLYING RADIOFREQUENCY ENERGY TO PERFORMED COLLAGEN FILMS AND SHEETS

CROSS-REFERENCE TO RELATED APPLICATIONS

The present application is a continuation of application Ser. No. 08/370,552, filed on Jan. 9, 1995, now abandoned, which was a continuation of application Ser. No. 08/007,691, filed on Jan. 22, 1993, now abandoned, which was a continuation-in-part of application Ser. No. 07/832,171, filed on Feb. 6, 1992, now abandoned, which was a continuation-in-part of ampliation Ser. No. 07/654,860, filed on Feb. 13, 1991, now U.S. Pat. No. 5,156,613.

BACKGROUND OF THE INVENTION

1. Technical Field

The present invention relates to the use of an inert gas beam radio frequency ("RF") energy generating device for use in joining, repairing or reconstructing biological tissue. In particular, the present invention relates to a method of utilizing a welding rod filler material in combination with such RF energy to join, repair or rebuild biological tissue.

2. Background Art

Optical energy, in particular that generated by lasers, has been applied and utilized in the medical field for a variety of surgical purposes. The medical industry initially utilized industrial lasers for the destruction of tumors or surface lesions in patients. At that time, the lasers were relatively crude, high powered and ineffective for delicate internal biological applications.

Subsequently, a variety of cauterization techniques were developed utilizing either laser or RF techniques. Laser optical energy was also utilized to reduce the flow of blood in an open wound or in a surgically created incision: the optical energy being supplied in sufficient quantity to sear or burn the blood vessels thus sealing the open ends of the capillaries and preventing blood flow. A typical use of laser cauterization is described in U.S. Pat. No. 4,122,853. Again, the types of lasers utilized at that time provided very high power application and very high wattage with the surrounding tissue also being destroyed, thus causing longer healing times, infection and scarring.

As newer, lower powered lasers were developed, techniques were developed for atheroma ablation or other endarterectomy procedures for blood vessels. One such procedure is disclosed in U.S. Pat. No. 4,878,492. The $CO_2$, YAG and Excimer lasers all provided substantial improvements in these procedures due to their lower power output. These more sophisticated devices each provide better aiming of a narrower optical energy beam such that destruction of the walls of blood vessels and tissues can be reduced. Also, advances in optical fiber technology allowed the surgeon to direct more accurately the optical energy to the desired location with greater precision.

Lasers have also been used to "glaze" the internal surfaces of blood vessels after balloon dilation and laser angioplasty in an attempt to prevent medical recollapse, intimal fibroplasia, and reobliteration.

Another procedure which has been developed includes the use of optical energy for welding or otherwise joining or connecting biological tissue. The original attempts to carry out these procedures began in the late 1960's and almost all universally met with failure not so much because of an inability to weld or join the tissue together, but because of the weakness of the resulting weld joint. The use of the lower powered laser devices, either alone or in combination with physiologic solutions, however, allowed the surgeon to cool the weld site sufficiently to obtain slight improvements in weld strength. Furthermore, RF energy has recently been utilized in both uni- and bi-polar generators to attempt to "weld" or "solder" biological tissue.

U.S. Pat. No. 4,672,969 discloses one method and apparatus for utilizing laser emitted optical energy to effect wound closure or other reconstruction of biological tissue by applying the optical energy to produce thermal heating of the biological tissue to degree suitable for denaturing the tissue proteins such that the collagenous elements of the tissue form a "biological glue" which seals the tissue to effect the joining. This glue is later reabsorbed by the body during the healing process. The patent discloses a number of different types of lasers with preference stated for the Nd:YAG type, because its particular wavelength allows optical energy to propagate without substantial attenuation through water and/or blood for absorption in the tissue to be repaired.

Fibrin, fibrinogen glue and albumin present a problem in that pooled plasma and other glues are almost universally contaminated with Hepatitis and HIV viruses. Albumin presents a similar problem. Thus, during an operation, it is common to use the patient's own fibrinogen to avoid this problem.

Despite these improvements, however, the weakness of the weld joint still remains as the primary disadvantage of this procedure and extensive current research is being conducted in an attempt to improve on that deficiency. My earlier U.S. Pat. No. 5,156,613 and application Ser. No. 07/832,171, now abandoned in favor of Continuation application Ser. No. 08/007,691, filed Jan. 22, 1993 each disclose the use of filler material, such as collagen, to improve the strength of the weld joint.

There are additional problems in the use of lasers for tissue welding. The amount of time needed to conduct laser welding repairs in surgery is relatively high. The time a surgeon needs to spend to learn how to use lasers is also high. The surgeon must wear cumbersome clothing and eye protection when using lasers, and this complicates the welding operation. Moreover, even with the most experienced surgeon with the best laser welding equipment, successful weld joints are achieved only about 75–80% of the time, and no one has offered a satisfactory explanation for the failures.

In addition, there are dozens of different lasers modalities available today, with many more being developed in an attempt to find those which will provide the most versatility in a variety of welding procedures. Currently, none of the modalities work for every type of surgery. Laser institutes have been established for surgeons to bring their patients to try to select the optimum modality for the particular procedure to be performed.

For the most part, however, endarterectomy, welding and joining have proven to be a problem. For example, intestinal welds have leaked in most instances. It is only in the case of subtle tissue ablation, e.g., retina, eye or skin, has the laser been repeatedly utilized with some measure of success. Use of the laser to replace the clip, suture or staple have not been consistently successful, and repairs to biological components such as muscle, tendon and nerve material have not been attempted.

I have now found that a particular form of RF energy is extremely useful for applying the filler material into the weld joint for a variety of biological components in a manner which promotes healing and which overcomes the shortcomings of the prior art.

SUMMARY OF THE INVENTION

The present invention relates to a method of joining or reconstructing biological tissue which comprises applying energy to the biological tissue using a particular form of RF energy while providing a suitable filler material thereto; denaturing or melting the filler material and adjacent biological tissue with the energy to cause mixing of the denatured or melted filler material and biological tissue, thus joining or reconstructing such tissue.

The applied energy is provided from an inert gas beam radio frequency welding device which has sufficient power dissipation to cause the energy or heat that is produced to be absorbed by the tissue and collagen filler material. The heat provided by the welding device is generally within a range bounded by the minimum absorption rate at which the protein elements of the tissue and collagen filler material are converted to melted collagen and by a maximum absorption rate which would cause water in the tissue or collagen filler material to boil. Thus, the protein elements of the tissue and the collagen filler material can be melted or denatured, mixed or combined, fused and then cooled to form a weld joint.

This device is operated at between about 20 and 120 watts, more preferably between about 35 and 80 watts, for about 1 to 60 and preferably 5 to 30 seconds, so that about 20 to 1800 joules, preferably about 100 to 1200 joules, are provided to make the weld joint. This amount of energy has been found to produce acceptable welds.

The filler material is preferably collagen and no special techniques are needed to place the collagen filler in the vicinity of the area to be welding. Generally, biological tissue is negatively charged, while the collagen material is positively charged. Thus, the collagen material is attracted to the tissue, where it can temporarily adhere until contacted by the energy beam.

Optionally, although not necessary, the collagen filler material may be adhesively attached to the biological tissue to assure proper placement thereupon. This may be achieved by applying the collagen material adjacent the biological material with fibrin glue or other biological tissue adhesive. In most instances, the electrostatic charge is sufficient to approximate welding material and biological tissue.

This method may also include applying an energy absorption aid to one of the filler materials or the biological tissue, or both, to facilitate absorption of the applied energy thereby. Generally, the energy absorbing aid is applied to preselected locations prior to the application of energy thereto, and it also assists in visually determining the areas to be joined or reconstructed. Preferred energy absorbing aids include blood, saline, plasma, or dyes such as Vital Green or Basic Red. Of course, blood is the most preferred energy absorbing aid because it has electrolytes and hemoglobin which absorb the particular wavelength of the argon beam, and it is often present when the tissue is being repaired.

Often, the biological tissue includes an incision. The method of the invention enables the surgeon to enclose the incision by placing a patch of collagen material over or onto the incision, held in place by electrostatic attraction, heating the tissue and patch with the energy beam, and joining the incision by the mixing of the denatured or melted filler material and biological tissue. For welding of complex tissue components, a fixture or other tool can be used to retain the patch adjacent the incision to assist in the welding operation and assume that the melted filler material is placed properly so that it can mix with denatured tissue to form the weld joint.

The filler material may be prepared by dissolving a predetermined amount of collagen material in water to form a solution, followed by drying or freeze drying of the solution in the desired form and shape of the collagen filler material. Preferably, the collagen material used to prepare the filler material is a mixture of an insoluble collagen material and a soluble collagen material in a weight ratio of about 1:3 to 3:1. The present method also contemplates applying an acceptable solution to one of the collagen filler materials or the biological tissue to control the temperature of the joint due to the energy imparted thereto. Blood and saline are considered to be optimum materials for this purpose.

When the biological tissue includes a lesion, the method further comprises forming a seal of collagen material near or upon the lesion. When the lesion comprises at least two separated segments of biological tissue, the method further comprises placing the two segments of tissue in close proximity, and guiding the energy source and collagen filler material into the area of their junction for joining or reconstruction thereof.

BRIEF DESCRIPTION OF THE DRAWINGS

The features and advantages of the present invention are more readily understood when read in conjunction with the attached drawing figures wherein.

DETAILED DESCRIPTION OF THE PREFERRED EMBODIMENTS

Figure 1:
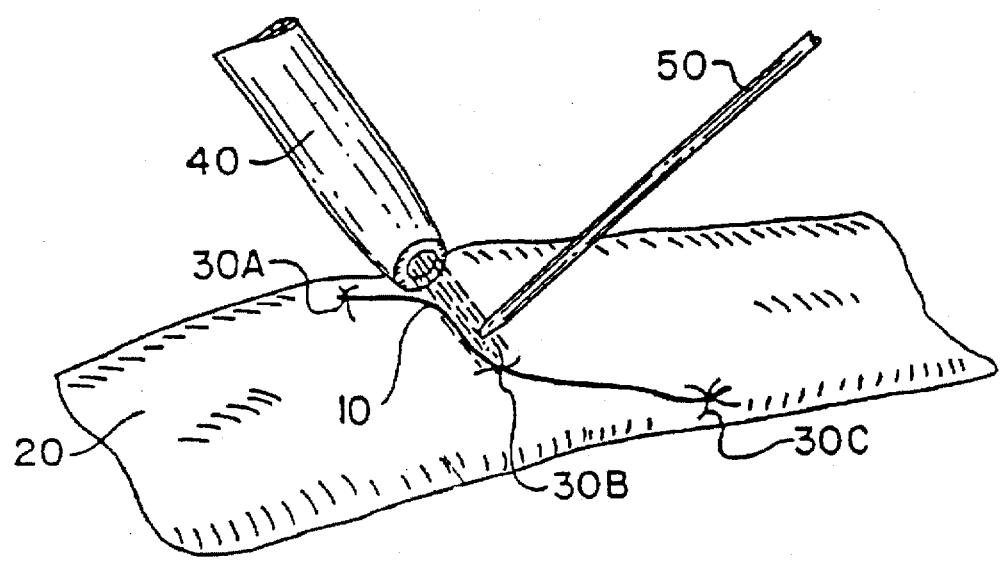
FIG. 1 is a perspective view of the use of a collagen welding rod for closing an incision in a blood vessel with the use of a inert gas beam RF welding device.

It is well known that biological tissue includes cell layers in a protein framework which provides tensile strength. The proteins are amino acids, and it is known that the application of heat or optical energy can denature such proteins. When the source of heat or energy is removed, the proteins if not totally broken down cool and begin to reconfigure and form an approximate replication of the prior tissue structure.

The prior art teaches that the application of energy from a laser could be used to bring the temperature of the biological tissue above room temperature but below the boiling point of water (preferably between 45°–75° F. and more preferably 60°–70° F.). The denaturing of collagen, a major source of protein in the human body, can also be achieved by the application of energy, and is believed to go into solution and form a type of "biological glue" which seals the incision or discontinuity in the biological tissue. Thus, it is theoretically possible to seal lesions, anastomose a severed or incised vessel or to reconstruct diseased or damaged tissue.

As noted above, there have been numerous difficulties and failures in obtaining successful tissue welds using lasers most likely due to the difficulties in using such devices, their relatively high energy input and slow energy absorption (i.e., inefficiency), as well as the lack of sufficient material in the joint which causes a lack of tensile strength. I have now found the optimum combination of energy source, filler material and flux which highly simplifies such welding procedures and enables almost any surgeon to successfully weld different types of tissue without having to first spend inordinate amounts of time learning how to use the process.

The most preferred energy source which is used to provide the desired energy for effecting the weld repair is an argon beam radio frequency tissue desiccator which is made by Birtcher Laboratories. This device, which is now renamed as an argon beam radio frequency photowelder, provides an easily controllable energy source of radio frequency activated argon gas which is utilized to fuse the filler material and surrounding tissue to form the weld joint. A tungsten filament, at a very high radio frequency, ionizes the argon gas flow from a jet nozzle, which leads to a relatively high energy transfer at relatively low temperatures. This makes it possible to apply a useful amount of energy to the tissue to be repaired at relatively low temperatures.

This device may be operated at 20–120 watts for about 1–60 seconds with an argon gas flow of 2–10 liters per minute. Preferably, the device is operated for 5–30 seconds at between 35–80 watts at an argon gas flow rate of 4–6 liters per minute. This provides a total amount of energy on the order of about 100–1200 joules for optimum fusion of the collagen welding rod materials and surrounding tissue, to produce fused joints having a distraction strength of between about 5 and 150 grams.

While argon gas is preferred, other inert gases can be used instead of argon. Also, other related inert gas beam radio frequency welding devices are available and can be used by one skilled in the art to achieve results similar to those presented herein.

I have previously found that a major disadvantage of the welding procedures used for rejoining incised tissue is that insufficient tissue material is present for completing a successful joint. When the applied energy actually denatures or melts the tissue in the areas to be joined, a portion of the tissue thickness is reduced so that the denatured materials can flow towards each other and stick together to form the joint. On relatively thin sections of tissue to be joined, such as in repairing an incised blood vessel wall, there is insufficient denatured material in the joint area for providing a sound, high tensile strength connection.

Collagen is known for use in the medical field as a material for repairing tissue damage caused by thermal, chemical or mechanical trauma (see, e.g., "Collagen: Its Place In the Medical Industry" by J. M. Pachence, et al., Medical Device and Diagnostic Industry, January, 1987). I have found that this material can be used as a filler material which can be placed in the path of the energy beam, melted or denatured, and directed into the incision or the tissue which is to be reconstructed. Based on qualitative and quantitative observations, the additional collagen molecules provided by the filler material allows the tensile strength of the welded incision to be significantly increased.

The application of RF energy and the use of additional specially prepared collagen material in the form of filler material as a welding rod provides several advantages in addition to increased tensile strength. The healing time of the wound is accelerated because blood supply to the affected tissue is reestablished via vascular invasion into the welded tissue immediately after the surgical procedure. The use of the present device provides an energy input that accelerates this procedure. In addition, little or no scarring is produced because sutures are eliminated or substantially minimized. Furthermore, the various techniques disclosed herein enhance the accuracy of the welding procedure thus avoiding RF energy damage to adjacent or unintended areas of such tissue.

A wide variety of materials may be used as a filler in this welding procedure. The most common source is collagen which may be obtained from bovine hides. Another material, which is ideal from the standpoint of melting, flowing, and compatibility with biological tissue, is a collagen-like substance which has been modified by dissolving collagen in water and modifying the thusly dissolved collagen to render its surface charge effectively more positive than prior to modification. This material is well known and is disclosed, e.g., in U.S. Pat. No. 4,238,480. The modified collagen is freeze-dried to form a solid mass of gelatin. In accordance with the teachings of the present invention, this mass of gelatin, alone or in combination with other collagen material, may be formed in the shape of a rod, strip, film or flake and utilized as a filler in a laser welding procedure.

Other forms of collagen which are suitable for use in the present invention include Semed F, a collagen preparation manufactured in native fiber form without any chemical or enzymatic modifications, and Semed S, a lyophilized collagen powder extracted from fresh bovine hides. Each of these products is available from Semex Medical, Frazer, Pa. The Semed F material is a Type I collagen (greater than 95%), while the Semed S is a mixture of Type I and Type III collagen macromolecules in which the shape and dimension of tropocollagen in its natural helical orientation is retained.

Either of the Semed S and Semed F collagen material may be formed into welding filler material by suspending a suitable amount (usually between about 0.5 and 10 weight percent) of the material in deionized water to form a viscous solution followed by drying the solution under the action of heat or by freeze-drying of the solution, followed by vacuum treating and heating steps. As above with the gelatin material, the final shape of the material can be in the form of a rod, strip, powder, etc. A paste formulation may also be formed by dissolving relatively large amounts of the material in relatively small amounts of saline or deionized water.

The shapes of these formed materials are solid and soft but firm. These materials may be readily sliced or cut to the desired sizes for use in the laser welding procedure. Also, the desired size and shape can be achieved by freeze-drying the material in a suitably sized mold which is configured to the desired size and shape of the product. The thicknesses of the rods or sheets can be between ¼ and 2 mm, depending upon the size of the incision to be joined or area of tissue to be reconstructed. When the paste form is utilized, it may be painted or dropped onto the ares of tissue to be joined or reconstructed. Thus, the surgeon can choose from a wide variety of shapes, sizes, densities, thicknesses and configurations of such filler material depending upon the type of tissue to be welded.

The concentration of the collagen in the liquid which is to be freeze-dried can range from 0.5–10% and preferably 1–5%, with the lower concentrations forming less dense or discontinuous solids. At lower concentrations of 0.5 to 1%, the Semed F forms a structure which approximates dense cobwebs.

Native collagen film, wherein the film strength is preserved and the triple-helix structure of the collagen polymer is maintained intact, can also be used, either alone or with a plasticizer incorporated therewith. A typical collagen sheet is cast from solution to a thickness of about 1.8 to 2 mm and contains the following composition by weight: collagen 70.3%, plasticizer (typically glycerol or glycerine) 16.9%, water 9%, other 3.8%. Such a material is available from Norwood Medical Products Division of Norwood Industries, Inc., Malverne, Pa.

When gelatin or other water soluble forms of collagen are utilized, certain advantages are provided in that the material will readily polymerize at body temperatures to form a stable subcutaneous gel. In addition, when implanted into the body as filler material in the weld joint, the polymerized material will become rapidly populated by host fibroblasts. Thus, the material becomes vascularized and can remain histologically, stable for up to 18 months. One problem with gelatin material per se, however, is that it is highly soluble in blood such that the flow of blood across the material will cause it to dissolve. Thus, gelatin or other soluble collagen material when used alone as laser weld filler should be limited to areas where direct contact with blood is avoided or minimized.

It is more advantageous to use mixtures of the various types of collagen to obtain the most desirable features of each grade. For example, a 50/50 mixture of Semed F and Semed S allows the joint to obtain the higher tensile strength values of the F grade while retaining the superior flow properties of the S grade. Proportions ranging from 3:1 to 1:3 also form useful mixtures. In addition, the gelatin material described above can be used in combination with the Semed F to achieve similar results.

Figure 2:
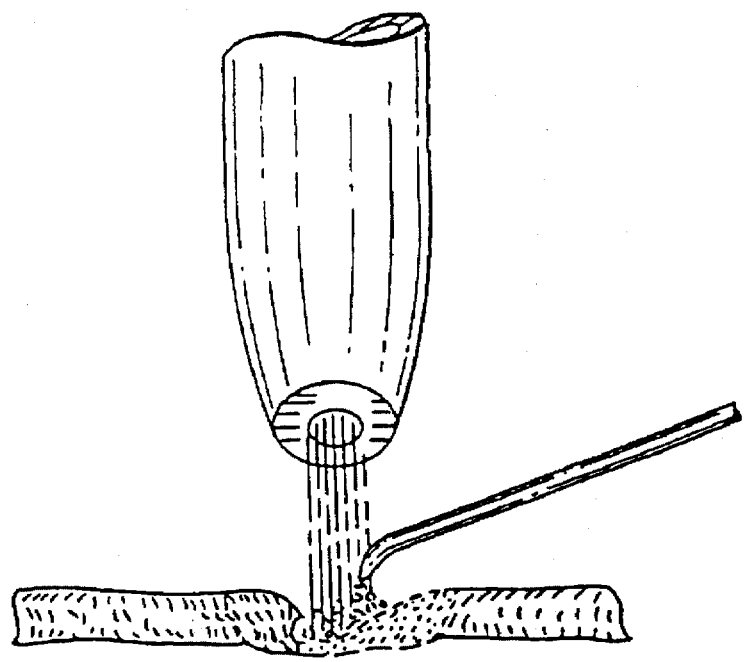
FIG. 2 is a detail of the denatured or melted collagen material in the weld joint of FIG. 1.

In addition, low melting polymers or polymeric materials such as copolymers of polyhydroxy butyric acid and valeric acid are useful in certain applications. Plasticizers such as polysaccharides may be included to further lower the melting point of these copolymers to below 200° F. These polymers may also be mixed with the collagen or gelatin to increase the strength of the final weld joint. The melting temperature of these polymers should be below about 212° F. and on the same order as the melting temperature of the collagen (i.e., between about 100°–200° F.). The protocol for the process is further appreciated by reference to FIG. 1. An incision 10 in a blood vessel 20 is closed by heating the tissue on either side of the incision with the photowelder 40. Filler material (e.g., collagen) is applied to the incision by placing the tip of welding rod 50 into the photowelder beam near the heated portion of the incision. The filler material 50 is literally melted (i.e., denatured) to provide additional collagen which flows onto or over the incision, mixes with the melted or denatured tissue, and thereafter cools and fuses with the underlying tissue substrate. Optionally, approximating sutures 30a, 30b and 30 may be used for deep or irregular incisions to place the tissue in adjacent relation. Also, a tool can be used to hold the tissue. FIG. 2 shows a detail of the joint as it is being made by this procedure.

As noted above, the collagen material is generally negatively charged, while the tissue is positively charged. The natural attraction of these oppositely charged components assists in their attraction and the proper placement of the filler material. Furthermore, the use of such additional collagen material allows the tensile strength of the joint to be significantly increased over weld joints which do not include additional collagen filler material. This difference in tensile strength is due to the fact that the collagen filler material provides an additional collagen molecular substrate specifically in the area to be joined. The present technique therefore is analogous to the plasma arc welding of metals such as steel or aluminum. In that process, additional filler metal is almost always used on thin sections. Since the biological tissue to be joined is often relatively thin, similar improvements are obtained when using a filler material than by attempting to make the joint without such filler material.

In an attempt to maintain the temperature of the tissue joint at a relatively low value, saline can be used. This is accomplished by dipping the collagen welding rod into saline prior to placing the saline dipped collagen welding rod adjacent to joint area or by dripping saline into the weld. In actual testing, saline cooling makes a difference of approximately 23° C. in the joint area (e.g., about 47° C. compared to about 70° C. without saline cooling).

The present invention resolves many of the problems of the prior art. When welding biological tissues, it is difficult to achieve uniformly good results. This problem is due in part to the inability of the surgeon to uniformly fuse the biological tissue on each side of the joint to obtain a satisfactory weld. With the use of collagen welding rod as proposed by the present invention, additional collagen material is supplied to the joint from the rod to compensate for any overmelting of tissue on either side of the joint. This also provides an abundance of additional material to seal voids or other defects caused by overheating of tissue. Thus, the reproducibility of the procedure and the attainment of uniform weld joints are significantly improved by the present invention.

All different types of biological tissue may be treated according to the present procedures. For example, all types of blood vessels, including veins, arteries, etc. in the vascular system can be connected or repaired, as can other ducts, muscle, fascia, tendon or skin.

Figure 3:
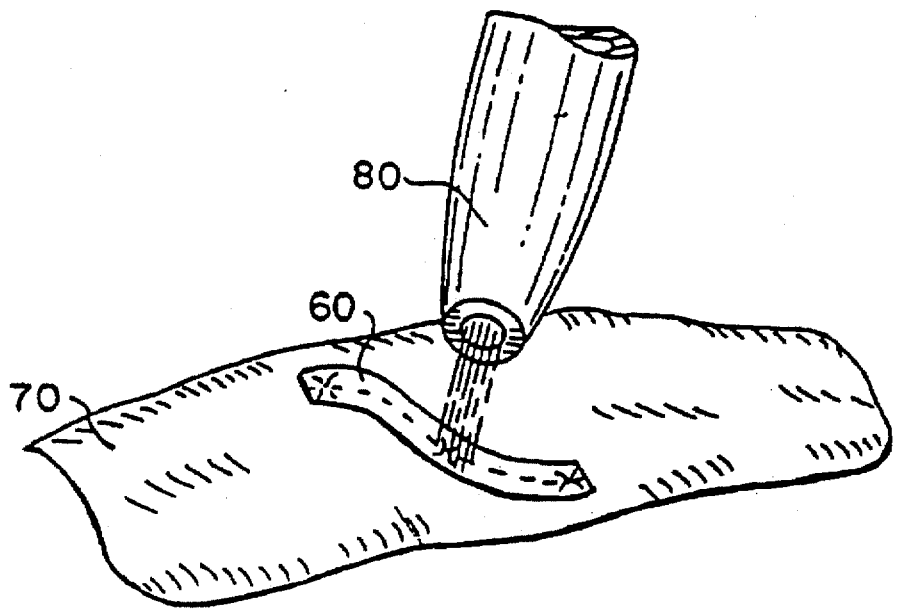
FIG. 3 is a perspective view of the use of a collagen strip or patch in the joining of an incision.
Figure 4:
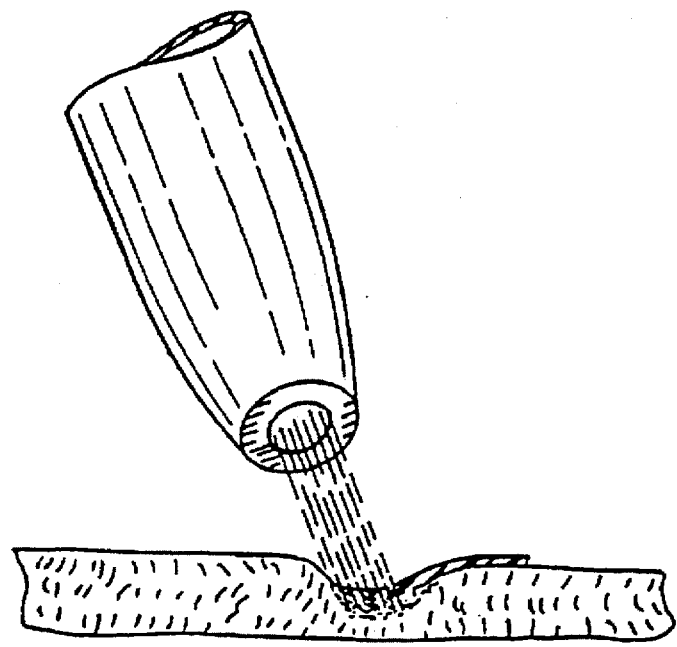
FIG. 4 is a detail of denatured or melted collagen material being applied upon a tissue defect or lesion.

Another procedure in accordance with the present invention is illustrated in FIG. 3. In that FIG., the incision is covered with a flat strip of collagen material 60 along its entire length. The adjacent blood vessel walls 70 on each side of the incision are overlapped by this strip 60 of collagen material. The negatively charged strip 60 is attracted to the positively charged tissue and is retained in the appropriate position by such attraction. The photowelder 80 fuses the strip of material to the adjacent blood vessel walls 70 by denaturing those materials into a mass which then solidifies to form the welded joint. Again, the use of the strip of collagen material 60 facilitates the welding operation and improves the resultant tensile strength of the weld joint. FIG. 4 shows a detail of the use of the strip material to fill a tissue defect or other lesion.

Optionally, the placement of the welding rod remains in the appropriate position for allowing denatured collagen to flow into the joint area can be achieved by securing or attaching the filler metal to the area to be joined. An easy way to accomplish this is to dip the filler material into fibrin glue prior to applying the filler material to the area to be welded. In addition to retaining the filler in the appropriate area desired, the fibrin glue or other biological tissue adhesive also appears to act as a flux which assists in directing the denatured or melted collagen material into the incision.

The welding procedure is made easier by utilizing a flux in conjunction with the filler material. These fluxes assist in the absorption of energy by the filler material so that the denaturing or melting process is more efficient, i.e., more of the energy is directly utilized to denature or melt the filler material rather than is scattered to other areas of the body near the tissue to be repaired.

Preferred fluxes include any of the numerous dyes, such as Vital Green or Basic Red. The color of the flux should match the wavelength of the transmitted energy for optimum results. For example, when the argon beam photowelder is used, brilliant green dye may be used because its wavelength is very close to that of an activated argon molecule. However, any substance, preferably which is in liquid form and which is capable of absorbing energy and transmitting the absorbed energy to the filler material, may be used. It is often convenient to simply use the blood or hemoglobin of the patient. Water, saline or other physiologic solutions are also useful and convenient due to their ready availability.

Advantageously, the flux is applied to the filler material to form a coating thereon. The filler material may simply be dipped into a reservoir of the flux. More complex arrangements, such as a spraying device or pump, can be used to apply the flux to the filler material, if desired.

In addition, the flux can be applied to the tissue to be repaired. This is easily accomplished, since the tissue is often bleeding to provide a suitable source of a preferred flux, i.e., blood. Also, the use of a dye is advantageous since it allows the joint to be more easily viewed by the surgeon to determine exactly where the welding procedure must be conducted.

A wide variety of filler material introduction devices can be used to place the welding material in the vicinity of the tissue to be repaired. For example, in addition to the above-described arrangements, a tube or rod of collagen welding material can be placed adjacent the energy beam. Thus, the surgeon can urge the tube or rod forward toward the distal end of the laser, where it can be melted by the energy beam. The tube can be dyed with a flux to assist in the melting procedure. As the end of the tube melts, the surgeon can urge further material into the path of the energy beam. To retain the area to be repaired in the proper position, a pair of grasping forceps can also be used.

In addition, for the repair of a blood vessel, a catheter or stent which includes a tubular covering of filler material can be introduced into the vessel beneath the area to be repaired. Thereafter, the laser welding procedure is conducted on the outside of the vessel, to melt both the vessel and the collagen material which is immediately below. Again, if desired, the collagen material can be dyed to increase its absorption of energy and melting efficiency.

In yet another embodiment, the welding procedure can be performed endoscopically: i.e., access to the area desired to be repaired or reconstructed can be made through multiple naturally or surgically created apertures: one aperture is used for insertion of the welder, another for the insertion of the filler material, and a third for monitoring the procedure with an optical fiber connected to an eye-piece or a video camera while the procedure can be visually observed through the eyepiece or camera, the presentation of the procedure on a monitor is preferred because the incision can be viewed in an enlarged mode so that the surgeon can accurately determine the proper placement of the filler material and completion of the joint.

EXAMPLES

The following examples illustrate applications of the Birtcher photowelder and certain filler materials on various tissues in accordance with the procedures of the present invention. The specific device used is known as the System 5000 Power Plus Electrosurgical Generator, and the Technical Manual for that device is expressly incorporated by reference herein to the extent necessary for understanding its operation.

Example 1

The results of reattaching or repairing tendons by welding were investigated in vitro. Beef tendons were obtained and segments were transsected. These segments were placed upon a conductor pad and pieces of filler material in a variety of configurations were placed adjacent the tendons to be welded. The filler material was placed in one of a number of positions and was made of different collagen substances and different configurations as shown in Table 1 for a series of welding operations. The area to be welded was wet with a flux, and then the energy beam was directed at the joint using 75 or 100 watts, a flow rate of argon of 4–6 liters per minute and for a time of about 4 to 18 seconds. These welds were produced quickly and easily, and exhibited relatively high tensile strength properties, as shown in Table 1.

In that Table, filler designated 5:2 is 5 parts Semed F and 2 parts Semed S as described above, while filler designated 3:2 is 3 parts Semed F and 2 parts Semed S. Filler size is given in cm for a sheet that is about 2 mm thick.

The results show that an increase in energy (i.e., use of higher wattage or longer welding times) generally produces higher tensile strength joints. Also, since the end of the tendon retracts slightly during the welding operation, the energy beam should be focused on the filler material than on the tendon. In addition to its use as a flux, saline also works well as a joint coolant. Blood or hemoglobin appears to be the most preferred flux. A device such as a C-clamp is useful in holding the materials to be welded in position.

TABLE 1

In Vitro Tendon to Tendon Welds

| Weld/ Technique | Energy (Watts) | Gas (L/min) | Filler Type/ Size | Time (sec) | Flux | Tensile Strength (g) | Joules |
|---|---|---|---|---|---|---|---|
| Top | 75 | 4 | 5:2/ 4 × 3 | 10 | Saline | 10 | 750 |
| Top | 75 | 4 | 5:2/ 5 × 2 | 18 | Saline | 20 | 1350 |
| Top | 75 | 4 | 5:2/ 4 × 2 | 8 | Saline | 5 | 600 |
| Top | 75 | 4 | 5:2/ 4 × 2 | 6 | Saline | 5 | |
| Side/Side | 75 | 4 | 5:2/ 4 × 2 | 4 | Saline | 20 | 450 675 |
| Side/Side (Layered) | 100 | 6 | 3:2/ 7 × 4 | 6 | Green Dye | 5 | 600 |
| Side/Side | 100 | 6 | 3:2/ 4 × 2 | 6 | Saline | 50 | 1600 |
| Side to Side and on top | 50 | 4 | 5:2/ 4 × 3 | 28 | Saline | 50 | 1400 |
| Top Lateral | 50 | 4 | 5:2/ 5 × 2 5:2/ 4 × 2 | 17 | Saline | 10–15 | 850 |
| Top only | 50 | 4 | 5:2/ 1 × 5 | 9 | Saline | 40–50 | 450 |
| Side to Side | 50 | 4 | 5:2/ 2 × 4 | 15 | Saline | 15–20 | 750 |
| Top | 75 | 4 | 5:2/ 6 × 3 | 8 | Saline | 15–20 | 600 |
| Top | 50 | 4 | 5:2/ 5 × 2 | 9 | Saline | 30–40 | 450 |
| Top | 40 | 4 | 5:2/ 8 × 2 | 14 | Saline | 50 | 560 |
| Top | 40 | 4 | 5:2/ 8 × 2 | 9 | Saline | 50 | 360 |

Example 2

The results of application of the Birtcher photowelder and certain filler materials on various tissues for a series of rats in vivo appear in Table 2. This technique was used to produce hemostasis in the left renal vein, the vena cava, a transsected spleen, a transsected achilles tendon, muscle and skin. These welds were produced quickly and easily, and exhibited high tensile strength properties.

As above, filler designated 5:2 is 5 parts Semed F and 2 parts Semed S, while filler size is given in cm for a sheet that is about 2 mm thick. All welds were successful and exhibited good tensile strength although specific values were not measured for each weld. The following day after the welding operation, the rats were observed to be moving about their cages with no visible side effects. At one and two weeks thereafter, the welded tendons were removed and examined, and the transsected area could not be distinguished from the remainder of the tendon. Although the weld strengths could not be measured in vivo, it was estimated to be above 50 and somewhere near 200 grams distraction strength. As shown in the results, these welds were produced with the photowelder on the order of seconds rather than the minutes which would be required for the use of laser welding devices. Thus, people with routine surgery and operating room skills can be expected to successfully apply these techniques to human patients.

TABLE 2

In Vivo Rat Tissue Welds

| Target Organ | Energy (Watts) | Gas (L/min) | Filler Type/Size | Time (sec) | Flux | Joules |
| --- | --- | --- | --- | --- | --- | --- |
| Left Renal | 40–42 | 4 | 5:2/2 × 2 | 1 | Blood | 40–42 |
| Spleen | 40–42 | 4 | 5:2/3 × 2 | 1–2 | Blood | 80–84 |
| Mid Line Incision | 40–42 | 4 | 5:2/4 × 3 | 8 | Blood | 320–336 |
| Mid Line Incision | 40–42 | 4 | 5:2/4 × 3 | 7 | Blood | 280–294 |
| Achilles Tendon (L. Leg) | 40 | 4 | 5:2/2 × 2 | 3–5 | Blood | 120–200 |
| Achilles Tendon (R. Leg) | 40 W | 4 | 5:2/2 × 2 | 3–5 | Blood | 120–200 |
| Vena Cava Incision | 40 | 4 | 5:2/2 × 3 | 10 | Blood | 400 |
| Mid Line Incision | 40 | 4 | 5:2/1 × 8 | 15 | Blood | 600 |
| Mid Line Incision | 40 | 4 | 5:2/1 × 8 | 15 | Blood | 600 |

Example 3

Photomicrographs of certain of the welds of Examples 1 and 2 are illustrated in the drawing figures. A description of each photomicrograph follows.

Figure 5:
FIGS. 5–16 are photomicrographs which show the morphology of various welded tissue joints immediately after welding and with passage of time during healing.
Figure 6:

FIGS. 5 and 6 are illustrations at 10X and 40X, respectively, of the in vitro tendon welds using a 5:2 filler material to a rat tendon in vitro. The welding device was operated at 75 watts for 4–5 seconds with a 7 liters/minute flow of argon, and the sample was taken one week after the weld joint was made. The smooth transition between the tendon and the filler material shows good bonding has occurred.

Figure 7:
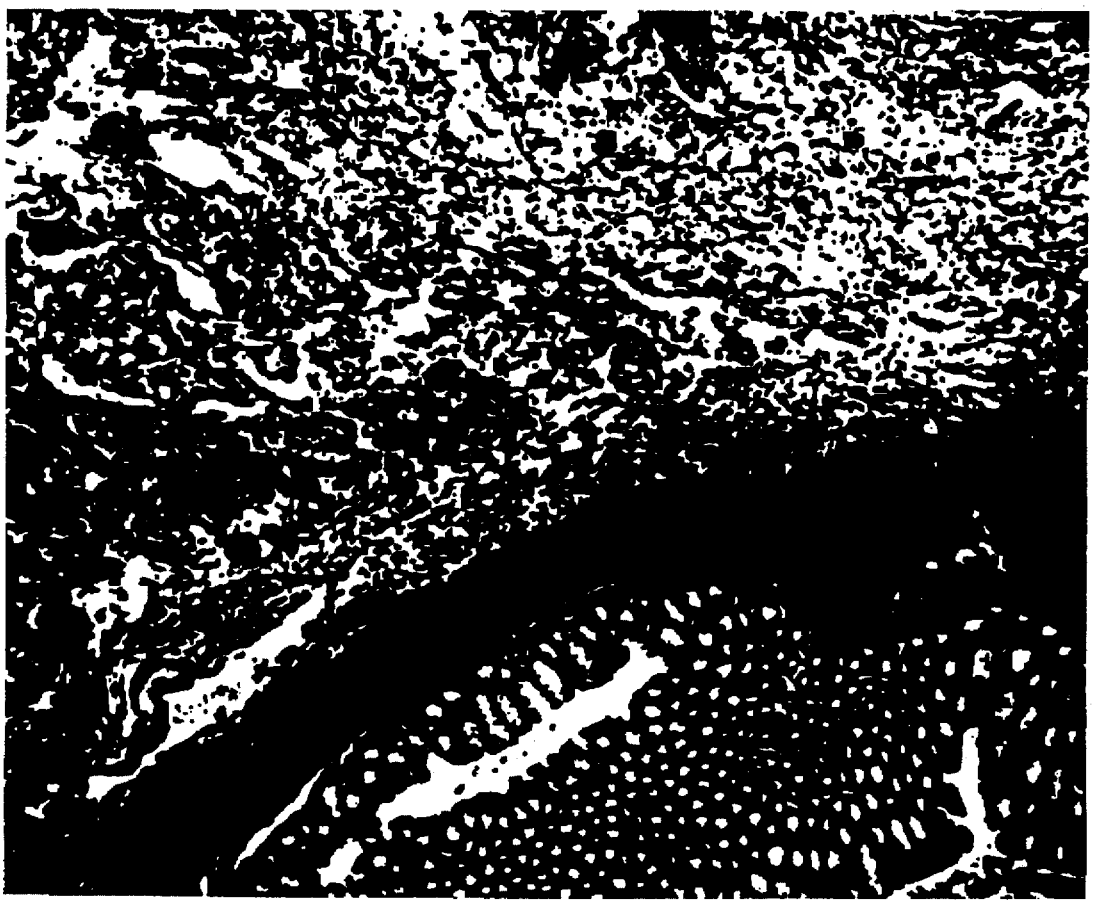
Figure 8:
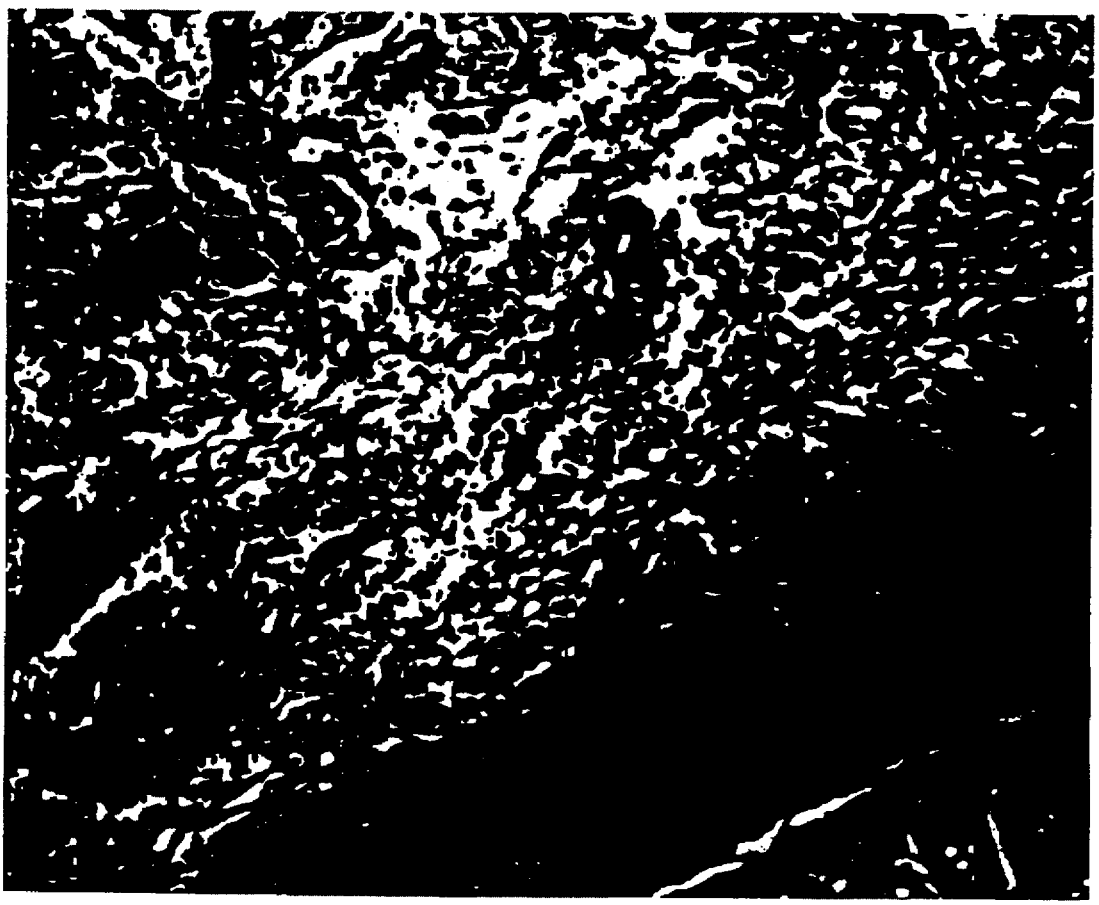

FIGS. 7 and 8 are illustrations at 10X and 40X, respectively, of the in vivo attachment of a 5:2 filler material to the capsule of a rat kidney. The welding device was operated at 50 watts for 2 seconds with a 4 liters/minute flow of argon, and the sample was taken one week after the weld joint was made. The granular response in the filler material consists primarily of fibroblasts and small blood vessels with very few giant cells being noted. The welded tissue displays intense vascularization.

Figure 9:
Figure 10:
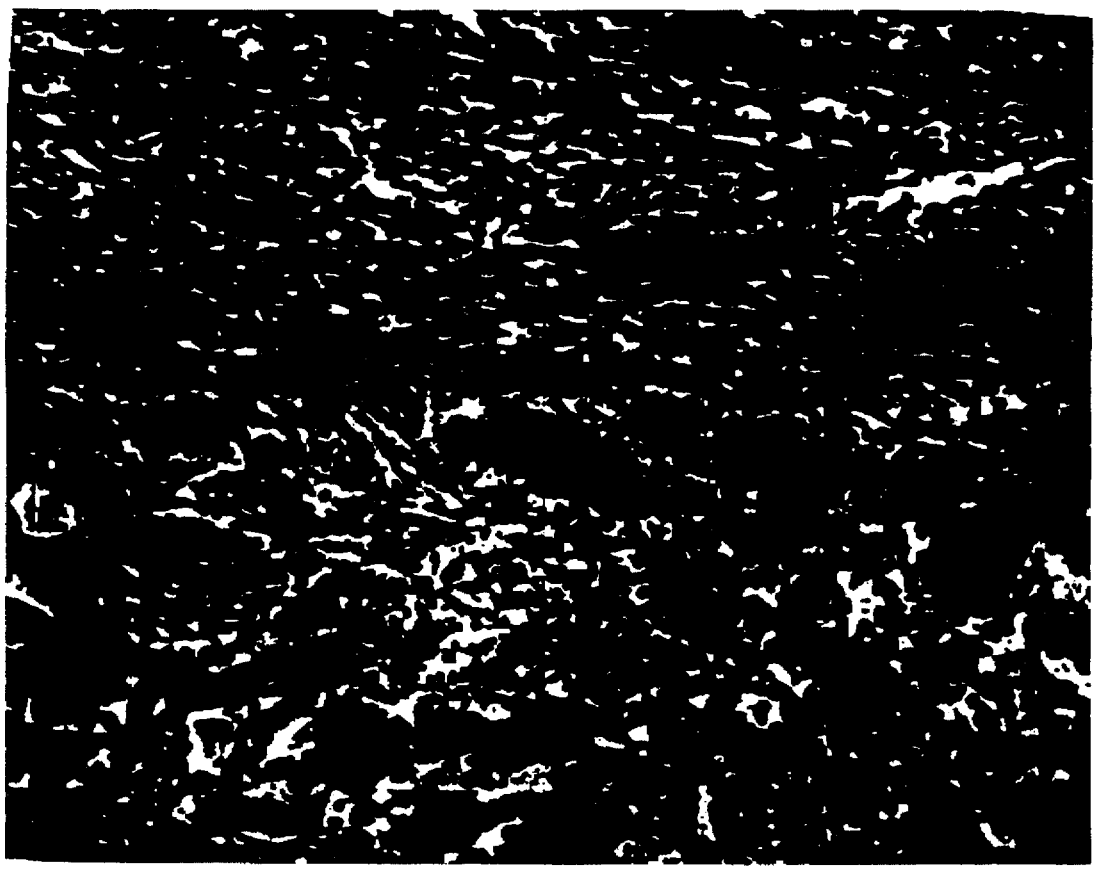

FIGS. 9 and 10 are illustrations at 10X and 40X, respectively, of the in vivo attachment of a 5:2 filler material to the gastronemious tendon of a rat. The welding device was operated at 40 watts for 2 seconds with a 4 liters/minute flow of argon, and the sample was taken 8 days after the joint was made. Note the continuous interface between the filler material and autologous tissue as well as the cellular infiltration into the filler material.

Figure 11:
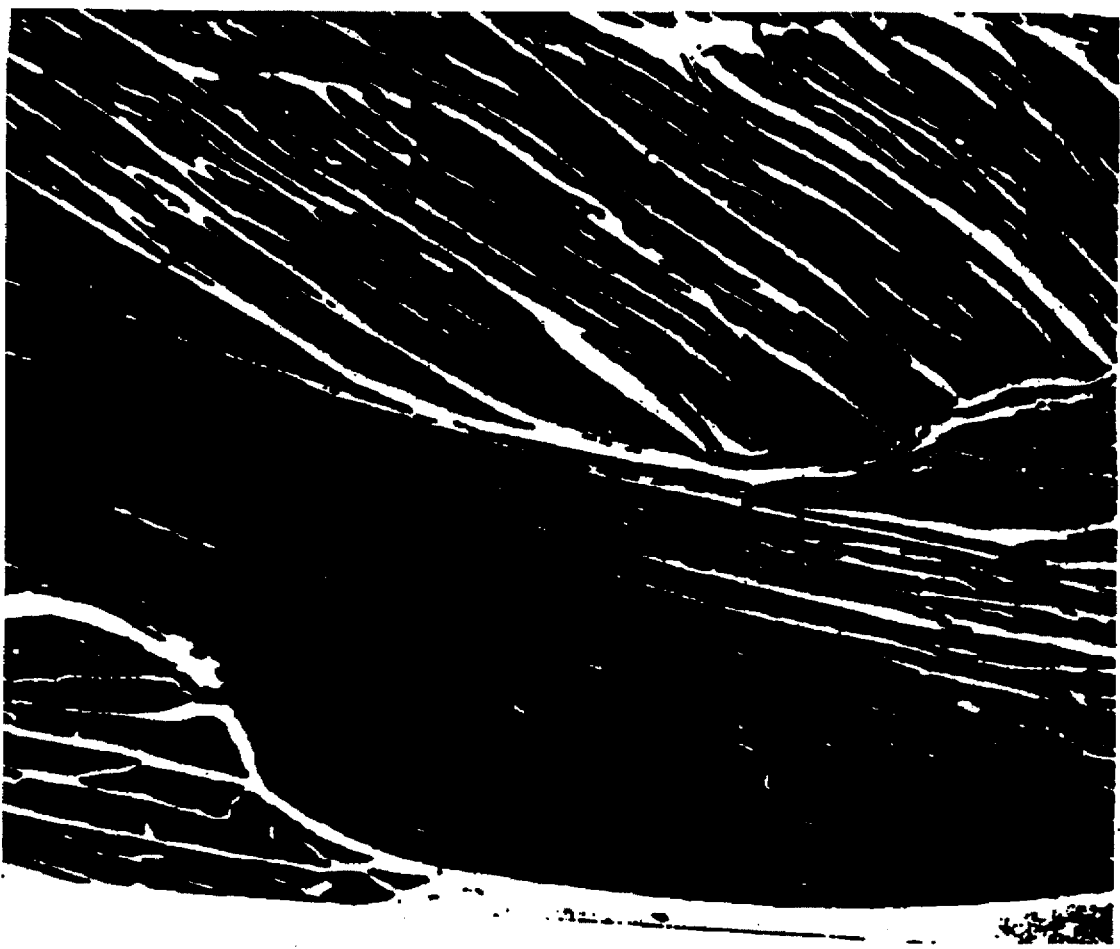
Figure 12:
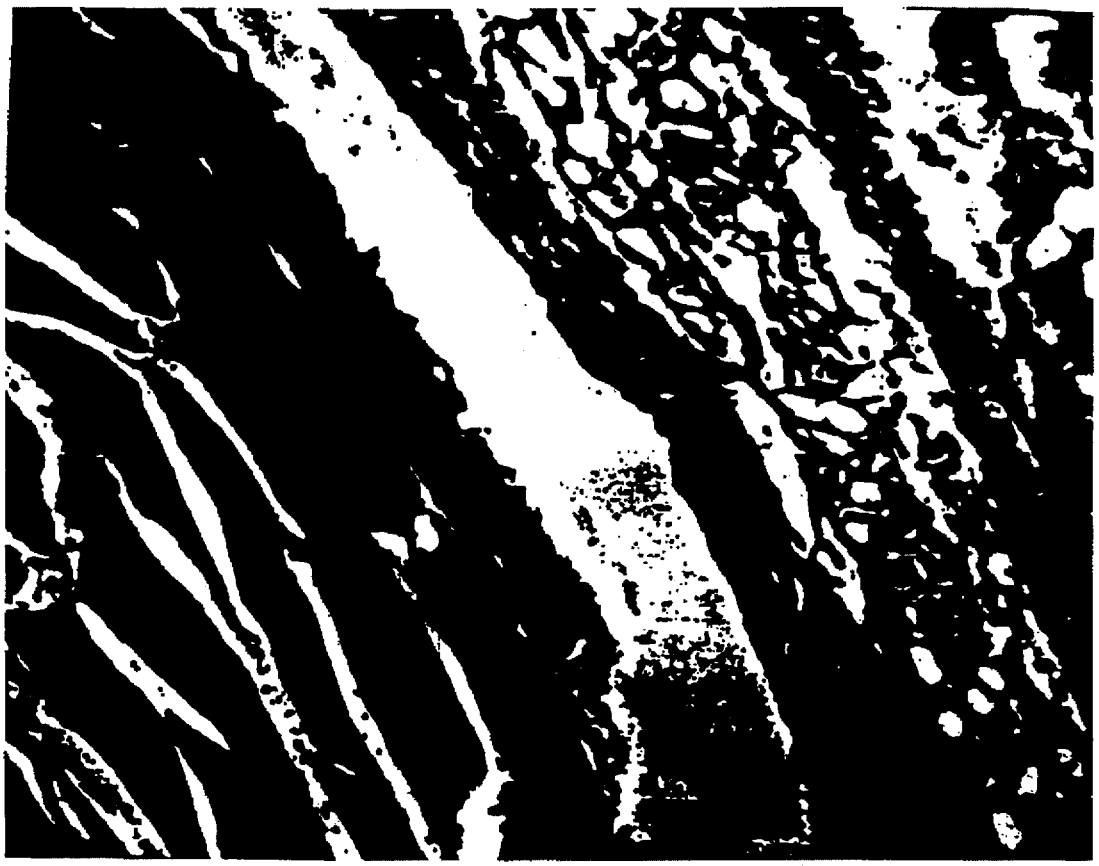
Figure 13:
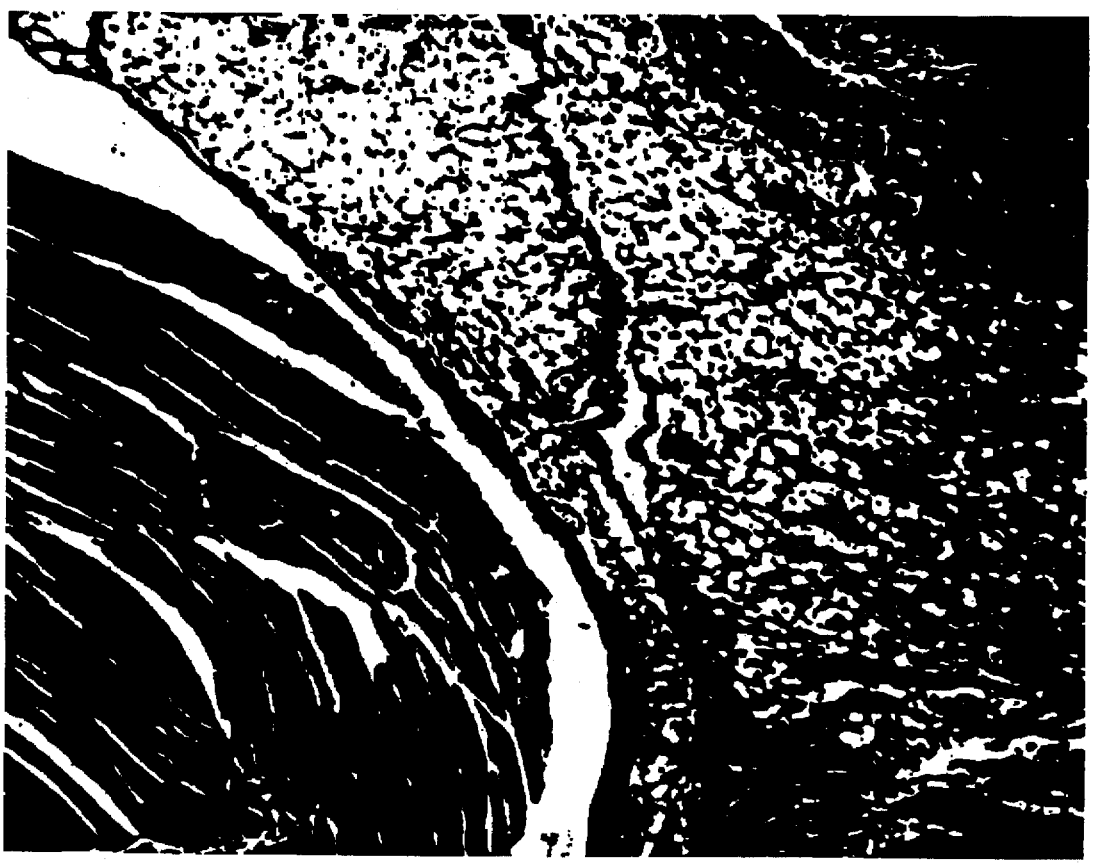

FIGS. 11, 12 and 13 are illustrations at 10X, 40X and 10X, respectively, of the in vivo attachment of a 3:2 filler material to the gastronemious tendon of a rat. The welding device was operated at 100 watts for 2–4 seconds with a 6 liters/minute flow of argon, and the sample was taken two weeks after the joint was made. Note the smooth interface between the filler material and autologous tissue as well as the appearance of cellular and vascular components in the filler material and the layer of mixed filler and tissue material against the musculature. The presence of vacuoles and granular response shows that vascularization and investment of the tissue is progressing.

Figure 14:
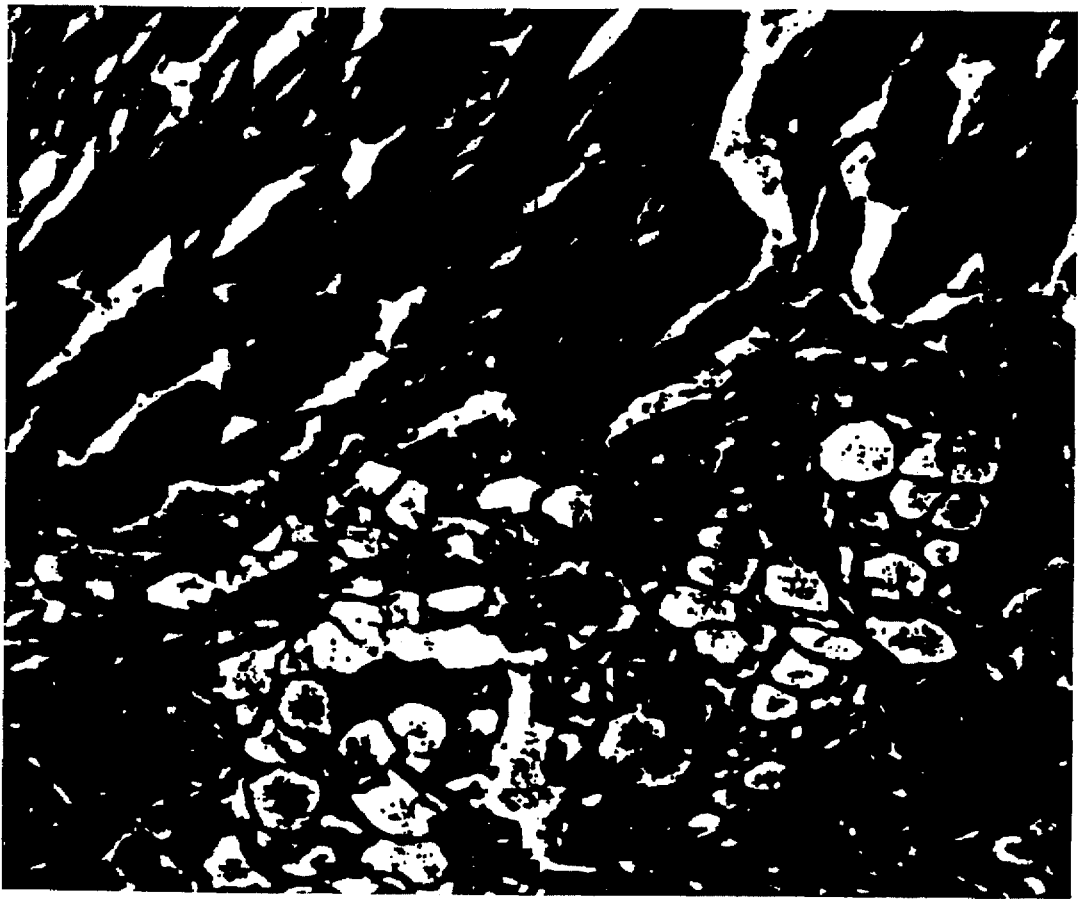
Figure 15:

FIGS. 14 and 15 are illustrations at 10X and 40X, respectively, of the in vivo attachment of a 5:2 filler material to muscle tissue of a rat. The welding device was operated at 75 watts for 8 seconds with a 4 liters/minute flow of argon, and the sample was taken two weeks after the weld joint was made. Note the cellular infiltration and vascularization of the filler material.

Figure 16:

FIG. 16 is an illustrations at 10X of the in vitro attachment of a 5:2 filler material to a beef tendon. The welding device was operated at 40 watts for 2 seconds with a 4 liters/minute flow of argon. Note the strong attachment between the filler material and the tendon as well as the absence of foreign body responses.

It is believed that numerous variations and modifications may be devised by those skilled in the art to the specifically disclosed invention, and it is intended that the appended claims cover all such modifications and embodiments as would fall within the true spirit and scope of the present invention.

What is claimed is:

1. A method of joining or restructuring tissue, said method consisting essentially of:
   providing a preformed film or sheet of a solid filler material which fuses to tissue upon the application of energy, wherein the film or sheet comprises collagen, gelatin, or a mixture thereof;
   placing the preformed film or sheet of filler material over the tissue to be joined or restructured; and
   applying radiofrequency energy at between about 20 and 120 watts to the filler material and the tissue after said filler material has been placed over the tissue for about 1–60 seconds, so that about 20–1800 joules are delivered to the filler material and tissue.

2. A method as in claim 1, wherein the radiofrequency energy is applied from an inert gas beam radiofrequency device.

3. A method as in claim 2, wherein the radiofrequency inert gas beam device is operated at between about 35 and 80 watts for about 5 to 30 seconds, so that about 100 to 1200 joules are delivered to the filler material and tissue.

4. A method of joining or reconstructing biological tissue, said method consisting essentially of:
   providing a preformed film or sheet of a solid filler material composed of collagen, collagen with a plasticizer, gelatin, gelatin with a plasticizer, or mixtures thereof;
   cutting the preformed film or sheet to a desired size;
   placing the cut film or sheet over the tissue to be joined or restructured; and applying radiofrequency energy to the cut film or sheet of filler material at between about 20 and 120 watts for about 1–60 seconds, so that about 20–1800 joules are delivered to the filler material and tissue.

5. A method of joining or reconstructing biological tissue, said method consisting essentially of:

providing a preformed film or sheet of a solid filler material composed of collagen, collagen with a plasticizer, gelatin, or gelatin with a plasticizer;

placing the preformed film or sheet over the tissue to be joined or restructured; and applying radiofrequency energy from an inert gas radiofrequency device at between about 20 and 120 watts to the film or sheet after said film or sheet has been placed over the tissue for about 1–60 seconds, so that about 20–1800 joules are delivered to the filler material and tissue.

\* \* \* \* \*

UNITED STATES PATENT AND TRADEMARK OFFICE
CERTIFICATE OF CORRECTION

PATENT NO. : 5,669,934

DATED : September 23, 1997

INVENTOR(S) : Philip N. Sawyer

It is certified that error appears in the above-identified patent and that said Letters Patent is hereby corrected as shown below:

Title page, item [54] and col. 1 line 3,

METHODS FOR JOINING TISSUE BY APPLYING RADIOFREQUENCY ENERGY TO PREFORMED COLLAGEN FILMS AND SHEETS

Signed and Sealed this

Thirteenth Day of January, 1998

Attest:

BRUCE LEHMAN

Attesting Officer

Commissioner of Patents and Trademarks